United States Patent [19]

Malis et al.

[11] Patent Number: 4,934,371
[45] Date of Patent: Jun. 19, 1990

[54] FETAL ELECTRODE PRODUCT

[75] Inventors: Michael J. Malis, Trumbull; Gilbert J. Neagle, West Haven, both of Conn.

[73] Assignee: American Home Products Corporation, New York, N.Y.

[21] Appl. No.: 351,609

[22] Filed: May 12, 1989

Related U.S. Application Data

[63] Continuation-in-part of Ser. No. 154,639, Feb. 9, 1988, abandoned.

[51] Int. Cl.5 .............................................. A61B 5/04
[52] U.S. Cl. ...................................... 128/642; 128/785
[58] Field of Search ............... 128/639, 640, 642, 785, 128/802, 786, 784, 419 P; 604/198

[56] References Cited

U.S. PATENT DOCUMENTS

| Re. 28,990 | 10/1976 | Hon et al. | 128/642 |
| 2,208,023 | 7/1980 | Ellis | 128/639 |
| 4,180,080 | 12/1979 | Murphy | 128/642 |
| 4,281,659 | 8/1981 | Farrar et al. | 128/635 |
| 4,321,931 | 3/1982 | Hon | 128/642 |
| 4,743,233 | 5/1988 | Schneider | 604/192 |
| 4,819,661 | 4/1989 | Heil, Sr. et al. | 128/634 |
| 4,836,208 | 6/1989 | Ulbrich | 128/642 |

FOREIGN PATENT DOCUMENTS 2738479 3/1979 Fed. Rep. of Germany ...... 128/642

*Primary Examiner*—Max Hindenburg
*Assistant Examiner*—John P. Lacyk
*Attorney, Agent, or Firm*—Darby & Darby

[57] ABSTRACT

A fetal electrode product comprises a guide tube, an electrode assembly having a spiral electrode extending from its forward end and a flexible drive tube extending through said guide tube adapted to engage said electrode assembly for axially moving and rotating said spiral electrode. A safety sleeve is retained on the forward portion of the electrode assembly to protect the doctor and mother from the pointed end of the spiral electrode before, during and after the electrode is removed from the fetus during birth.

4 Claims, 2 Drawing Sheets

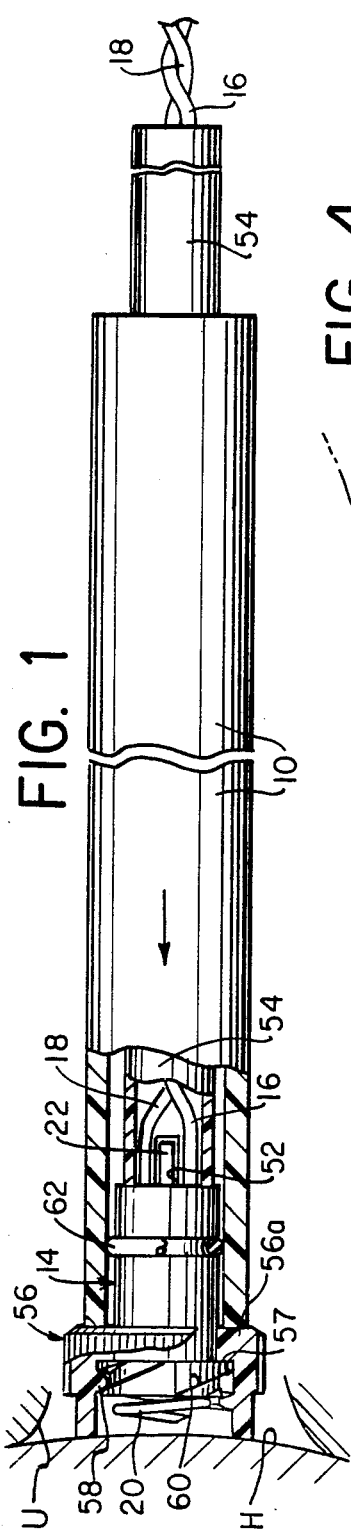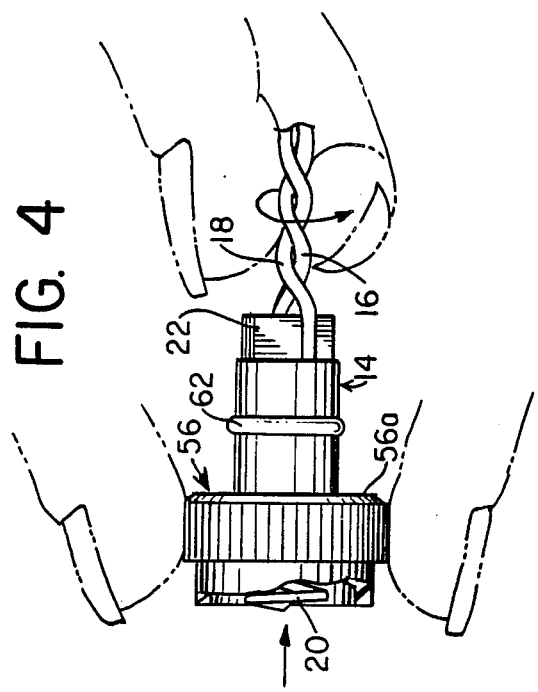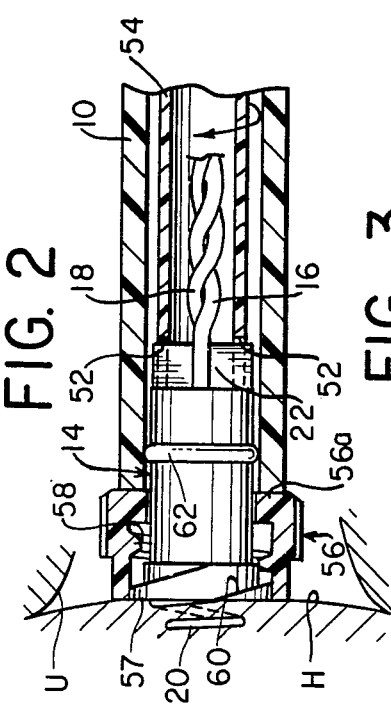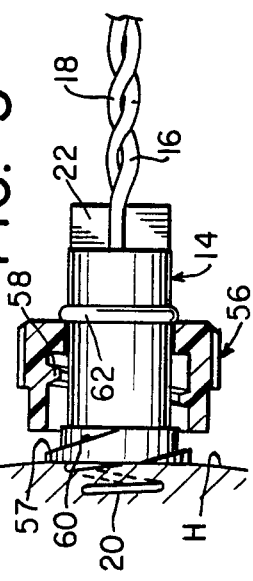

FETAL ELECTRODE PRODUCT

This application is a continuation in part application of application Ser. No. 154,639 filed on Feb. 9, 1988, now abandoned.

This invention pertains to fetal electrodes. More particularly, this invention relates to a safety feature for use with fetal electrodes of the type shown in U.S. Pat. No. Re. 28,990 of Hon et al reissued on Oct. 5, 1976.

BACKGROUND

FIGS. 8-10 of U.S. Pat. No. Re. 28,990 illustrate the fetal electrode most commonly used in the United States today. The product comprises a curved form sustaining guide tube through which an electrode assembly can be delivered to a fetal presenting part (typically the scalp) during delivery. The electrode which engages the fetus is a coil that extends from the forward end of an electrode holder and can be rotated by means of a flexible drive tube passing through the guide tube and adapted to engage a plate-like maternal electrode extending from the rear of the plastic holder.

The electrode is attached to the fetus by turning the drive tube causing the spiral electrode to penetrate the fetal presenting part. After the electrode is attached, the guide tube and drive tube are removed leaving the electrode in place. Wires attached to the coil and maternal electrode are then attached to a fetal monitor so that the condition of the fetus can be monitored prior to birth.

During birth, the coil is removed from the fetus by unscrewing it. When this is done, because the sharp point of the coil is unprotected, it can cause injury to the physician or the patient.

The object of this invention is to provide a safety device which can be used to sheath the coil of a spiral electrode to prevent injury to the patient and physician before, during and after the electrode is attached or removed from the fetus.

SUMMARY OF THE INVENTION

According to one embodiment of the invention, a protective cap is mounted on the electrode assembly of a spiral electrode. The cap is axially movable with respect to the spiral electrode so that it sheaths the electrode both during application of the electrode and removal.

In a second embodiment, a safety sleeve is mounted on the electrode assembly and is axially moveable with respect to the spiral electrode from a fully extended to a retracted position. The safety sleeve, whether in an extended or retracted position, is biased toward the extended position and sheaths the electrode before, during and after attachment and removal.

THE DRAWINGS

FIG. 1 is a side elevational view, partially in section, showing a first embodiment of the invention;

FIG. 2 is a corresponding view of the first embodiment of the invention after the coil has been attached to the fetal presenting part;

FIG. 3 shows the electrode in place after the drive tube and guide tube have been removed;

FIG. 4 shows how the operator positions the protective cap of the first embodiment in accordance with the invention to sheath the coil when the electrode is to be removed;

DETAILED DESCRIPTION

Figure 5:
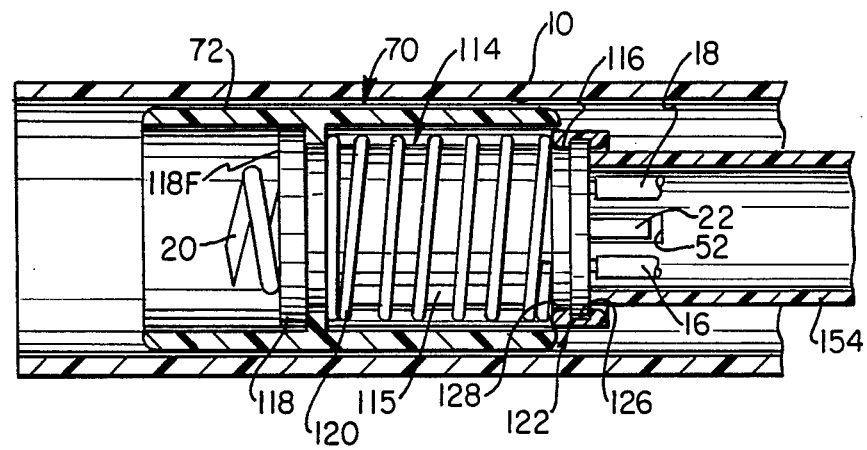
FIG. 5 is a sectional view of a second embodiment of the invention showing the spiral electrode sheathed by the outer casing of the safety sleeve which is positioned within the guide tube.

A guide tube constructed in accordance with the invention can be used with electrodes other than the spiral electrode shown in the '990 patent; however, since that is the preferred version of the electrode it is illustrated in the drawing.

Referring to FIGS. 1-4, the electrode product includes a guide tube 10 having an open forward end through which a holder member 14 is adapted to pass. The holder member 14 has a spiral electrode 20 mounted in its forward end and a flat maternal electrode 22 mounted in its rear end.

The diameter of the cylindrical holder member 14 approximates the inner diameter of guide tube 10. Consequently, the holder member prevents lateral movement of the electrode coil 20 (relative to the guide tube) while the coil is being attached to the fetus. Moreover, the length of the holder member 14 is such that when the spiral electrode 20 extends just beyond the end of the guide tube 10 (for attachment to the fetus), the cylindrical holder member within the guide tube prevents skewing of the coil. These features help to reduce the possibility of injury to the fetus when the electrode is being applied.

A first electrode wire 16 extends through the rear end of the holder member 14 and is electrically connected to the rear end of spiral electrode 20. A second electrode wire 18 also extends through the rear end of holder member 14 and is electrically connected to the forward end of the second electrode 22.

Both electrodes 20 and 22 are preferably constructed of stainless steel and are soldered to their respective electrode wires 16 and 18. The holder member 14 is made of an insulating material, such as plastic, and electrically isolates the electrodes 20 and 22 from one another.

A flexible drive tube 54 is slidably and rotatably disposed in the guide tube 10 for rotating the holder 14 to screw the spiral electrode 20 into a fetal epidermis. The forward end of the drive tube 54 is provided with a pair of slots 52 which are adapted to receive the rearwardly extending portion of the plate electrode 22. When the slots 52 on the forward end of the drive tube 54 engage the plate electrode 22, the holder 14 and spiral electrode 20 may be rotated by rotating the flexible drive tube 54.

A cylindrical grip (not shown) may be attached to the rear of drive tube 54. The electrode wires 16 and 18 extend rearwardly through a releasable wire clamp (not shown) at the back of the drive tube 54 which extends from the rear portion of the guide tube 10 for connection to a suitable apparatus (not shown) for monitoring fetal heartbeat.

According to the first embodiment of the invention, a protective cap 56 is mounted on the holder member 14. In this embodiment which is shown in FIGS. 1-4, the protective cap 56 may be cylindrical in shape and long enough to extend just beyond the sharp point of coil 20.

The holder member 14 includes an enlarged forward head portion 57 which contains a helical groove 60. The groove 60 mates with a complementary helical rib 58 on the interior surface of the cap 56 to retain the cap in its protective position and cause axial movement of the two parts when one is rotated relative to the other. As best shown in FIGS. 2 and 3, the closed end 56a of the cap 56 fits snugly on the holder member 14. When rib 58 and groove 60 are disengaged, longitudinal movement of holder member 14 relative to the cap 56 away from the fetus (i.e., movement of cap 56 to the left) is limited by abutment of the head 57 against the top 56a of the cap. A retaining ring 62 extends circumferentially around the holder member 14 toward the rear thereof. The ring 62 protrudes slightly to function as a stop or retainer abutting against the top 56a of cap 56 to limit its rearward movement (i.e., movement of cap 56 to the right) on the holder member when rib 58 and groove 60 are disengaged.

FIGS. 1-4 also illustrate the first embodiment in actual use, with the fetal presenting part (typically the head) indicated by the letter H and the mother's uterus by the letter U. The physician receives the fetal electrode product with the cap 56 in the position shown in FIG. 1, i.e., with rib 58 threadedly engaging groove 60 so that cap 56 sheathes coil 20. With the spiral electrode 20, holder 14 and plate electrode 22 disposed as shown in FIG. 1, the doctor inserts the cap 56 and guide tube 10 through the woman's vagina and cervix until the forward end of the cap 56 makes contact with the fetal head (or other portion of the fetus). Using cap 56 as a stabilizing platform, the physician then applies the electrode by rotating the drive tube 54. As shown in FIG. 2, the rotation of the holder member 14 causes the coil 20 to engage and penetrate the fetus H. As the holder member 14 rotates with cap 56 stationary, the threaded engagement of rib 58 and groove 60 causes axial displacement of cap 56 relative to holder member 14 until the rib 58 and groove 60 are disengaged, at which point cap 56 can then slide on holder member 14. After the electrode is in place, guide tube 10 and drive tube 54 are removed in conventional fashion. The protective cap 56 will stay in place because of the ring 62 (see FIG. 3). During birth, when it is desired to remove the electrode from the fetus, the physician grasps the cap 56 with one hand (FIG. 4) and twists the wires 16 and 18 with the other hand to unscrew the coil from the fetus. As the coil is rotated, groove 60 is threaded back onto the helical rib 58 of protective cap 56 until the coil is once again sheathed by cap 56. Hence, the electrode coil is not likely to contact either the physician or the mother and the electrode can be removed without fear of injury.

Figure 7:
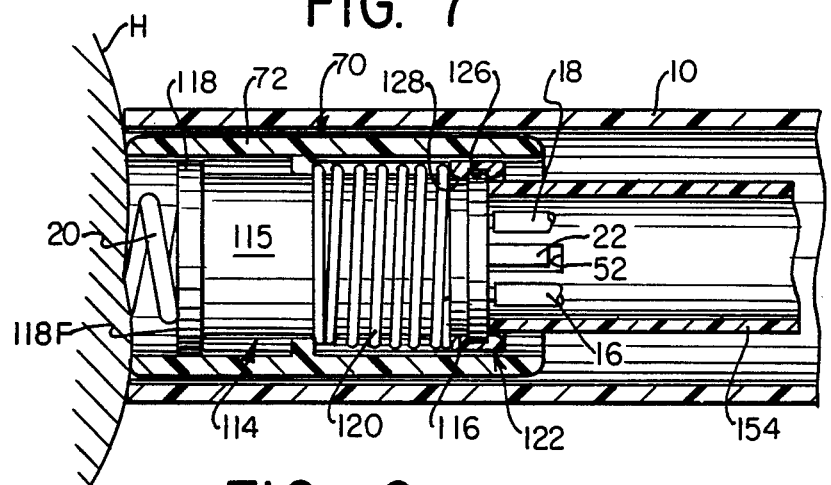
FIG. 7 is a sectional view of the second embodiment showing the spiral electrode in contact with the fetal epidermis.
Figure 6:
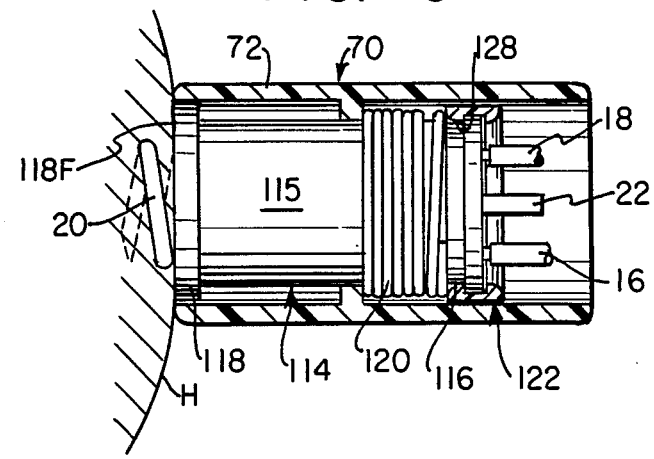
FIG. 6 is a sectional view of the second embodiment showing the spiral electrode attached to and secured within the fetus.

In the second embodiment of the invention shown in FIGS. 5-7, holder member 14 which is shown in FIGS. 1-4 is replaced by a modified holder member 114 having a shoulder 118 at its forward end and a groove 116 towards its rearward end. Holder member 114 like holder member 14 is made of insulating material which electrically isolates the electrodes from one another. A safety sleeve 70 is shown in FIGS. 5-7 with an outer casing 72. Safety sleeve 70 sheaths spiral electrode 20 whenever the electrode is not secured in the fetal epidermis. Relative axial movement between outer casing 72 and holder member 114 is permitted as with protective cap 56 and holder member 14 of the first embodiment. An annular projection 124 extends substantially orthogonally from the inner wall of outer casing 72 to mate with the cylindrical body 115 of electrode holder 114. Annular projection 124 slides along body 115 when a force is applied axially to outer casing 72. A snap ring 122 having recess 126 and latching edge 128 is secured in groove 116 by pressure fit. Spring 120 is coiled around holder 114 and trapped between annular projection 124 and snap ring 122.

FIG. 5 shows outer casing 72 in its fully extended sheathed position around electrode 20 within the forward end of guide tube 10. Drive tube 154 is shown at the rearward end of holder member 114.

The other elements and features of the second embodiment are essentially the same as those described in the first embodiment and are denoted using the same numerical designation. Thus, guide tube 10, spiral electrode 20, second electrode 22, first and second electrode wires 16 and 18, and slots 52 which receive electrode 22 to rotate holder 114 and screw spiral electrode 20 into a fetal epidermis are all provided in the second embodiment and shown in FIG. 6. FIG. 6 also shows spiral electrode 20 secured to the epidermal tissue of the fetus with the outer casing in a retracted position in which spring 120 is compressed between annular projection 124 and snap ring 122.

FIGS. 5-7 also illustrate the second embodiment in actual use. During insertion, the physician places guide tube 10 (within which is safety sleeve 70 which sheaths electrode 20 as is shown in FIG. 5) through the vagina and cervix of a woman to make contact with the fetal presenting part. When guide tube 10 makes contact with the fetal presenting part, the physician holds guide tube 10 stationary and pushes the rear end of drive tube 154 forward so that outer casing 72 makes contact with the fetal presenting part. The physician continues to apply pressure to the rear end of drive tube 154 causing spiral electrode 20 to move toward the fetal presenting part until the electrode makes contact with the fetal presenting part as shown in FIG. 7.

When the physician feels that contact by electrode 20 with fetal presenting part has been made, he rotates drive tube 154 as in the first embodiment and thereby attaches electrode 20 into the fetal epidermis. Spring 120 has an appropriately sized spring modulus which enables the physician to feel when electrode 20 has contacted the fetus.

As shown in FIG. 6, as electrode 20 is driven into place, electrode holder 114 moves axially toward the fetal presenting part until front face 118F of shoulder 118 comes into contact with the fetal presenting part. The axial movement of holder 114 towards the fetal epidermis and the attachment of electrode 20 causes spring 120 to become further compressed between annular projection 124 and snap ring 122 as shown in FIG. 6. Once the spiral electrode 20 is attached, guide tube 10 and drive tube 154 can be removed leaving electrode 20 surrounded by outer casing 72 of safety sleeve 70 and connected to the fetal epidermis.

From the moment when insertion of the fetal electrode product commences through the moment of complete attachment of the fetal electrode product (FIG. 6), outer casing 72 of safety sleeve 70 surrounds and sheaths electrode 20.

When it is desired to remove electrode 20 from the fetus such as when monitoring is complete or after birth, the physician grasps electrode wires 16 and 18, twisting them counterclockwise and thereby unscrewing electrode 20 from the fetal epidermis as in the first embodiment of the invention. As electrode 20 is unscrewed, outer casing 72 remains in contact with the fetal epidermis, and shoulder 118 and front face 118F move axially away from the fetal epidermis causing the gradual release of compression of spring 120. Upon the complete removal of electrode 20 from the fetal epidermis, the compressive force within spring 120 is simultaneously released causing spring 120 to quickly expand, which in turn causes shoulder 118 and electrode 20 to be pulled further away from the fetal epidermis into the sheathed protection of outer casing 72, thereby avoiding possible accidental puncture to the fetus, mother, and physician. Since the point of electrode 20 need not be capped or recapped by the physician, there is a further decrease in the risk of accidental puncture.

While the present invention has been particularly shown and described in reference to two preferred embodiments thereof, it will be understood by those skilled in the art that various changes in form and details may be made therein without departing from the spirit and scope of the invention.

We claim:

1. A fetal electrode product for attachment to a fetus, comprising:
    a guide tube;
    an electrode assembly having a holder member with a rearward end and a forward end and a spiral electrode extending in a forwardly direction from said forward end;
    a flexible drive tube extending through said guide tube and adapted to engage said electrode assembly for axially moving said holder member and for rotating said spiral electrode; and
    a safety sleeve having an outer casting adapted to envelop said holder member and move axially relative to said holder member between a first position, where the casing is fully extended to sheath the spiral electrode and holder member, and a second position, where the casing retracts from the first position allowing the spiral electrode to be attached to the fetus while continuing to sheath the holder member, said safety sleeve further including a means for biasing said outer casing toward said first position.

2. A fetal electrode product as in claim 1 wherein the biasing means includes a spring coiled around the holder member.

3. A fetal electrode product as in claim 2 wherein the forward end of the holder member has a shoulder, the rearward end of the holder has a groove, and further including a snap ring which is secured within the groove.

4. A fetal electrode product as in claim 3 wherein the safety sleeve has an inner surface, and said inner surface has an annular projection which extends substantially orthogonally from said inner surface.

* * * * *